(12) United States Patent
Ferree

(10) Patent No.: US 6,340,369 B1
(45) Date of Patent: Jan. 22, 2002

(54) TREATING DEGENERATIVE DISC DISEASE WITH HARVESTED DISC CELLS AND ANALOGUES OF THE EXTRACELLULAR MATRIX

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 09/638,726

(22) Filed: Aug. 14, 2000

Related U.S. Application Data

(60) Provisional application No. 60/148,913, filed on Aug. 13, 1999.

(51) Int. Cl.⁷ ................................................. A61F 2/44
(52) U.S. Cl. .......................... 623/17.11; 623/17.16; 623/919; 424/93.7
(58) Field of Search .................... 623/17.11–17.16, 623/919, 908; 424/93.7

(56) References Cited

U.S. PATENT DOCUMENTS

| | | | | |
|---|---|---|---|---|
| 4,801,299 A | * | 1/1989 | Brendel et al. .......... | 623/16.11 |
| 5,464,439 A | * | 11/1995 | Gendler ................... | 623/16.11 |
| 5,514,180 A | * | 5/1996 | Heggeness et al. ...... | 623/17.11 |
| 5,545,229 A | * | 8/1996 | Parsons et al. .......... | 623/17.11 |

OTHER PUBLICATIONS

Steven Frick MD, SPINE vol. 19 No. 16, pp 1826–1835 1994.*

* cited by examiner

Primary Examiner—David H. Willse
Assistant Examiner—Suzette J. Jackson
(74) Attorney, Agent, or Firm—Gifford, Krass, Groh, Sprinkle, Anderson & Citkowski, PC

(57) ABSTRACT

Living intervertebral disc cells are harvested, cultured and combined with type-specific collagen-glycosaminoglycan extracellular matrix analogues to restore disc function and eliminate pain in patients with disc disease. In the preferred embodiment, the engineered disc tissue is morselized to allow insertion through a small puncture in the annulus fibrosis with a needle and syringe. Additional therapeutic substances such as culture medium, growth factors, differentiation factors, hydrogels polymers, antibiotics, anti-inflammatory medications, or immunosuppressive medications are disclosed as additives to the engineered disc tissue.

35 Claims, No Drawings

TREATING DEGENERATIVE DISC DISEASE WITH HARVESTED DISC CELLS AND ANALOGUES OF THE EXTRACELLULAR MATRIX

REFERENCE TO RELATED APPLICATIONS

This application claims priority of U.S. provisional patent application Ser. No. 60/148,913, filed Aug. 13, 1999, the entire contents of which are incorporated herein by reference.

FIELD OF THE INVENTION

This invention relates generally to the treatment of diseased or traumatized intervertebral discs, and more particularly, to the use of engineered disc tissues in conjunction with such treatment.

BACKGROUND OF THE INVENTION

Intervertebral discs provide mobility and a cushion between the vertebrae. At the center of each disc is the nucleus pulposus which, in the adult human, is composed of cells and an insoluble extracellular matrix which is produced by the nucleus itself. The extracellular matrix is composed of collagen, proteoglycans, water, and noncollagenous proteins.

The cells of the nucleus pulposus have chondrocyte-like features. Blood vessels do not course into the nucleus pulposus. Rather, the cells of the nucleus pulposus of the adult human obtain nutrients and eliminate waste by diffusion through blood vessels in the endplates of the vertebrae adjacent to the disc.

The nucleus pulposus is surrounded by the annulus fibrosis, which is composed of cells (fibrocyte-like and chondrocyte-like), collagen fibers, and non-fibrillar extracellular matrix. The components of the annulus are arranged in 15–25 lamellae around the nucleus pulposus.

To date, the treatment of degenerative disc disease has relied for the most part on eliminating the defective disc or disc function. This may be accomplished by fusing the vertebra on either side of the disc. In terms of replacement, most prior-art techniques use synthetic materials to replace the entire disc or a portion thereof. My pending U.S. patent application Ser. No. 09/415,382 discloses disc replacement methods and apparatus using synthetic materials.

Unfortunately, disc replacement using synthetic materials does not restore normal disc shape, physiology, or mechanical properties. Synthetic disc replacements tend to wear out, resulting in premature failure. The problems associated with the wear of prosthetic hip and knees are well known to those skilled in orthopedic surgery. The future of treating degenerative disc disease therefore lies in treatments which preserve disc function. If disc function could be restored with biologic replacement or augmentation, the risk of premature wear out would be minimized, if not eliminated.

SUMMARY OF THE INVENTION

This invention resides in a method of treating a diseased or traumatized intervertebral discs using natural, engineered tissue as opposed to synthetic materials. Broadly, live, intervertebral disc cells are harvested from a patient, cultured, and transplanted while still viable into the affected disc. In the preferred embodiment, the cultured cells are transferred and grown on an analogue of the extracellular matrix to yield an engineered disc tissue. Collagen-glycosaminoglycans preferably provide the extracellular matrix, though existing alternative and yet-to-be-developed analogues may be substituted.

Depending upon the target region of the recipient, the cells preferably differentiate into nucleus pulposus like cells, annulus fibrosis like cells, or both. To assist in differentiation, the nucleus pulposus like cells may be combined with type II collagen-glycosaminoglycans, and the annulus fibrosis like cells may be combined with type I collagen-glycosaminoglycans.

The cells or engineered tissues may be introduced using any surgical technique, including percutaneous or laparoscopic approaches. As one delivery mechanism, a passageway may be formed through the annulus fibrosis, with the cells or engineered disc tissue being introduced into the disc through the passageway. In particular, the engineered disc tissue may be morselized and injected into the disc with a needle and syringe or through a small cannula.

The method of the invention may further include the step of adding one or more therapeutic substances to the cells prior to transplantation. Such therapeutic substances could include culture media, growth factors, differentiation factors, hydrogels, polymers, antibiotics, anti-inflammatory medications, immunosuppressive medications, or any useful combination thereof.

DETAILED DESCRIPTION OF THE INVENTION

Autologous nucleus pulposus chondrocyte like cells are obtained by aspiration or biopsy of healthy discs of the patient. Other humans and recently deceased human or animal donors may alternatively be used, including fetal sources, preferably having a familial relationship to minimize or avoid the need for immunosuppressive substances. Guidelines for tissue procurement including surgical technique of removal, number of hours between death of the donor and tissue procurement, and testing of the donor for infectious disease, are well described in the literature.

The harvested cells are then isolated and cultured using standard techniques. A recent study highlighted the role played by the environment on the cells cultured. Chondrocytes grown in a matrix of type II collagen retained their chondrocyte features and synthesized materials for the extracellular matrix. Chnodrocytes grown in a matrix of type I collagen developed fibroblastic features and produced less material for the extracellular matrix.

The harvested sterile nucleus pulposus is preferably morselized and washed with phosphate buffered saline. The cells are released from the extracellular matrix with 0.2% clostridial collagenase (Worthington CLS II, 140 u/mg) and agitated. See Klagsburn, "Methods in Enzvmology, Vol. VII. The resulting suspension is filtered with a 153.mu.g nylon sieve (Tetko, Elmford, N.Y.).

The filtered solution is then centrifuged at 1800 rpm to remove the cells. The supernatant above the cells is removed with a micropipette until the cell concentration reaches 5.times.10.sup.7 cells/cc. The harvested cells are grown in Hamm's F-12 culture media, 10% fetal calf serum, L-glutamine (292.mu.g/cc), penicillin (100 u/cc), streptomycin (100.mu.g/cc), and ascorbic acid (5.mu.g/cc) at 37.degrees C. The above method is described in detail in U.S. Pat. No. 6,060,053, which is incorporated in its entirety herein by reference. The cells of the annulus fibrosis are harvested and cultured using similar techniques.

The cultured cells are then transferred and grown on an analogue of the extracellular matrix. Nucleus cells are preferably grown on a porous type II collagen-glycosaminoglycan matrix. Annulus fibrosis cells are preferably grown on a type I collagen-glycosaminoglycan matrix. Techniques to form the analogue extracellular matrices have been described previously. For example, Bovine type I collagen is precipitated from and acid dispersion with chondroitin-6-sulfate. The precipitated collagen is spread onto a flat surface or injected into a 3.8 mm (inside diameter) silicone tube. The collagen is then cooled and freeze dried. The matrices can be cross-linked by dehydrothermal treatment, ultraviolet light, and using aldehydes or other crosslinking agents. The final matrix is 95% porous. The average pore diameter is 30–120 um. A matrix using type II collagen is similarly formed.

Precursor cells of nucleus pulposus cells or annulus fibrosis cells, chondrocytes, or other living cells that could function like nucleus pulposus cells or annulus fibrosis cells or that could differentiate into cells to build a functional nucleus pulposus or annulus fibrosis could also be used.

The cultured cells, preferably along with the reconstructed extracellular matrix, are injected into the affected disc. The extracellular matrix may be morselized to fit through a small cannula or needle. The fibers of the lamella alternate direction between layers. A blunt tipped needle or cannula could be forced through the annulus. Upon withdraw of the needle, after injecting the transplanted nucleus pulposus, the separated fibers of the lamella would return to their normal position, sealing the annulus. The cultured cells and engineered extracellular matrix of the annulus fibrosis may be injected into the annulus fibrosis. Those skilled in the art will realize the needle could be directed into the posterior or lateral portion of the disc percutaneously with fluoroscopic guidance and into the anterior portion of the disc laparoscopically.

In the preferred embodiment, the transplanted nucleus is added to the patient's nucleus pulposus. Alternatively, the patient's nucleus may be removed with standard techniques (enzymatically (chymopapain) or with the aid of a laser, suction device, shaver, or other surgical instrument). If the nucleus is removed, the hole in the annulus should be small to facilitate closure at the end of the procedure.

Additional therapeutic substances may be added to the transplanted nucleus. For example, resorbable culture medium, tissue growth or differentiation factors (recombinant generated morphogenetic proteins, PDGF, TGF-$\beta$, EGF/TGF-$\alpha$, IGF-I, $\beta$FGF), hydrogels, absorbable or nonresorbable synthetic or natural polymers (collagen, fibrin, polyglycolic acid, polylactic acid, polytetrafluoroethylene, etc.), antibiotics, anti-inflammatory medication, immunosuppressive medications, etc. could be beneficial.

I claim:

1. A method of treating a diseased or traumatized intervertebral disc having a nucleus and annulus fibrosis, comprising the steps of:

harvesting live, intervertebral disc cells;

combining the harvested cells with an analogue of the extracellular matrix to produce an engineered disc tissue; and transplanting the engineered disc tissue into the disc.

2. The method of claim 1, wherein:

the harvested cells are nucleus pulposus cells, precursors of nucleus pulposus cells, or cells capable of differentiating into nucleus pulposus cells; and the harvested cells are transplanted into the nucleus of the disc.

3. The method of claim 1, wherein:

the harvested cells are annulus fibrosis cells, precursors of annulus fibrosis cells, or cells capable of differentiating into annulus fibrosis cells; and the harvested cells are transplanted into the annulus fibrosis of the disc.

4. The method of claim 1, further including the steps of:

morselizing the engineered disc tissue;

forming a passageway through the annulus fibrosis; and transplanting the engineered disc tissue into the disc through the passageway.

5. The method of claim 1, further including the step of adding one or more therapeutic substances to the engineered disc tissue.

6. The method of claim 5, wherein the therapeutic substances include one or more of the following:

culture media, growth factors, differentiation factors, hydrogels, polymers, antibiotics, anti-inflammatory medications, or immunosuppressive medications.

7. The method of claim 1, wherein the step of transplanting the engineered disc tissue into the disc includes injecting the engineered disc tissue into the disc through a needle and syringe or small cannula.

8. The method of claim 1, wherein the step of transplanting the engineered disc tissue includes percutaneously or laparoscopically injecting the engineered disc tissue into the disc being treated.

9. The method of claim 1, further including the step of keeping the harvested cells viable until placed into the disc being treated.

10. The method of claim 1, wherein the analogues of the extracellular matrix include collagen-glycosaminoglycans.

11. A method of treating a diseased or traumatized intervertebral disc, comprising the steps of:

harvesting live cells from a human or animal donor; and transplanting the harvested cells into the disc being treated while the harvested cells are still viable, wherein, subsequent to transplantation:
a) at least some of the cells differentiate into nucleus pulposus like cells,
b) at least some of the cells differentiate into annulus fibrosis like cells, or both a) and b).

12. The method of claim 11, further including the step of adding one or more therapeutic substances to the cells prior to transplantation.

13. The method of claim 12, wherein the therapeutic substances include one or more of the following:

culture media, growth factors, differentiation factors, hydrogels, polymers, antibiotics, anti-inflammatory medications, or immunosuppressive medications.

14. The method of claim 11, wherein the step of transplanting the cells includes the step of injecting the cells into the disc being treated with a needle and syringe or through a small cannula.

15. The method of claim 11, wherein the step of transplanting the cells includes the step of percutaneously or laparoscopically injecting the cells into the disc being treated.

16. The method of claim 11, further including the steps of:

combining the nucleus pulposus like cells with type II collagen-glycosaminoglycans; and combining the annulus fibrosis like cells with type I collagen-glycosaminoglycans.

17. The method of claim 11, further including the steps of:

combining the harvested cells with an analogue of the extracellular matrix to create an engineered disc tissue; and transplanting the engineered disc tissue into the disc being treated.

18. The method of claim 17, further including the steps of:

morselizing the engineered disc tissue;

forming a passage into the disc being treated through the annulus fibrosis;

inserting the engineered disc tissue into the disc through the passageway.

19. The method of claim 17, wherein the analogues of the extracellular matrix are collagen-glycosaminoglycans.

20. A method of preparing engineered intervertebral disc tissue, comprising the steps of:

harvesting live intervertebral disc cells;

combining the harvested cells with an analogue of the extracellular matrix to produce an engineered disc tissue; and keeping the engineered disc tissue viable until use.

21. Engineered disc tissue prepared according to the method of claim 20.

22. The engineered disc tissue of claim 21, wherein:

the harvested cells are nucleus pulposus cells, precursors of nucleus pulposus cells, or cells capable of differentiating into nucleus pulposus cells; and the harvested cells are transplanted into the nucleus of the disc.

23. The engineered disc tissue of claim 21, wherein:

the harvested cells are annulus fibrosis cells, precursors of annulus fibrosis cells, or cells capable of differentiating into annulus fibrosis cells; and the harvested cells are transplanted into the annulus fibrosis of the disc.

24. The engineered disc tissue of claim 21, wherein the constituents are morselized.

25. The engineered disc tissue of claim 21, further including one or more therapeutic substances.

26. The engineered disc tissue of claim 25, wherein the therapeutic substances include one or more of the following:

culture media, growth factors, differentiation factors, hydrogels, polymers, antibiotics, anti-inflammatory medications, or immunosuppressive medications.

27. The engineered disc tissue of claim 21, wherein the analogues of the extracellular matrix include collagen-glycosaminoglycans.

28. A method of preparing engineered intervertebral disc tissue for subsequent transplantation, comprising the steps of:

harvesting live cells from a human or animal donor wherein, following transplantation:
a) at least some of the cells differentiate into nucleus pulposus like cells,
b) at least some of the cells differentiate into annulus fibrosis like cells, or
c) both a) and b);

combining the nucleus pulposus like cells with type II collagen-glycosaminoglycans; and combining the annulus fibrosis like cells with type I collagen-glycosaminoglycans.

29. Engineered intervertebral disc tissue prepared according to the method of claim 28.

30. The intervertebral disc tissue of claim 29, further including one or more therapeutic substances.

31. The method of claim 30, wherein the therapeutic substances include one or more of the following:

culture media, growth factors, differentiation factors, hydrogels, polymers, antibiotics, anti-inflammatory medications, or immunosuppressive medications.

32. A method of preparing engineered intervertebral disc tissue, comprising the steps of:

harvesting live cells from a human or animal donor; and transplanting the harvested cells into the disc being treated while the harvested cells are still viable, wherein, subsequent to transplantation:
a) at least some of the cells differentiate into nucleus pulposus like cells,
b) at least some of the cells differentiate into annulus fibrosis like cells, or c) both a) and b); and combining the harvested cells with an analogue of the extracellular matrix.

33. Engineered intervertebral disc tissue prepared according to the method of claim 32.

34. The intervertebral disc tissue of claim 33, further including one or more therapeutic substances.

35. The method of claim 34, wherein the therapeutic substances include one or more of the following:

culture media, growth factors, differentiation factors, hydrogels, polymers, antibiotics, anti-inflammatory medications, or immunosuppressive medications.

* * * * *

UNITED STATES PATENT AND TRADEMARK OFFICE
CERTIFICATE OF CORRECTION

PATENT NO.     : 6,340,369 B1
DATED          : January 22, 2002
INVENTOR(S)    : Ferree It is certified that error appears in the above-identified patent and that said Letters Patent is hereby corrected as shown below:

Title page,
Item [*] Notice, delete the phrase "by 0 days" and insert -- by 8 days --

Signed and Sealed this

Twenty-first Day of September, 2004

JON W. DUDAS
*Director of the United States Patent and Trademark Office*